(12) United States Patent
Uchiyama et al.

(10) Patent No.: US 8,070,864 B2
(45) Date of Patent: Dec. 6, 2011

(54) OXYGEN CONCENTRATOR

(75) Inventors: Mitsuru Uchiyama, Yamaguchi (JP); Katsushi Fujimoto, Yamaguchi (JP); Makoto Ando, Yamaguchi (JP)

(73) Assignee: Teijin Pharma Limited, Tokyo (JP)

( * ) Notice: Subject to any disclaimer, the term of this patent is extended or adjusted under 35 U.S.C. 154(b) by 274 days.

(21) Appl. No.: 12/310,890

(22) PCT Filed: Sep. 21, 2007

(86) PCT No.: PCT/JP2007/069119
§ 371 (c)(1), (2), (4) Date: Mar. 11, 2009

(87) PCT Pub. No.: WO2008/035817
PCT Pub. Date: Mar. 27, 2008

(65) Prior Publication Data
US 2009/0255403 A1    Oct. 15, 2009

(30) Foreign Application Priority Data

Sep. 22, 2006 (JP) ................................. 2006-256850
Feb. 16, 2007 (JP) ................................. 2007-036036

(51) Int. Cl.
*C01B 13/02* (2006.01)
*B01D 53/04* (2006.01)
(52) U.S. Cl. ................... 96/109; 96/116; 128/205.24
(58) Field of Classification Search ............. 95/23, 130; 96/109, 110, 116, 121, 130; 128/204.21, 128/205.21, 205.27, 205.24
See application file for complete search history.

(56) References Cited

U.S. PATENT DOCUMENTS

| 3,880,616 | A | * | 4/1975 | Myers et al. ...................... 95/26 |
| 4,584,001 | A | * | 4/1986 | Dechene ......................... 96/114 |
| 5,071,453 | A |   | 12/1991 | Hradek et al. |
| 5,137,549 | A |   | 8/1992 | Stanford et al. |
| 6,558,451 | B2 | * | 5/2003 | McCombs et al. ................. 95/98 |
| 6,712,877 | B2 | * | 3/2004 | Cao et al. .......................... 95/10 |

FOREIGN PATENT DOCUMENTS

JP   57-071804 A   5/1982
JP   03-063907 B2  10/1991

(Continued)

OTHER PUBLICATIONS

International Search Report mailed Oct. 30, 2007.

(Continued)

*Primary Examiner* — Frank Lawrence, Jr.
(74) *Attorney, Agent, or Firm* — Rader, Fishman & Grauer PLLC (57) ABSTRACT

An apparatus to provide an oxygen concentrator that is a pressure swing adsorption-type oxygen concentrator equipped with; at least one adsorption bed filled with an adsorbent capable of selectively adsorbing nitrogen relative to oxygen, an air supply device to supply compressed air to the adsorption bed, a flow channel switching device to repeat at a predetermined timing an adsorption step to supply air from the air supply device to the adsorption bed to isolate concentrated oxygen and a desorption step to depressurize the adsorption bed to regenerate the adsorbent therein, and a flow rate setting device to set a volume of concentrated oxygen supplied to a user; comprising an exhaust pipe channel equipped with a leak valve in a flow channel between the air supply device and the adsorption bed to release a part of compressed air that is to be supplied to the adsorption bed into atmosphere.

7 Claims, 6 Drawing Sheets

FOREIGN PATENT DOCUMENTS

| | | |
|---|---|---|
| JP | 08-133703 A | 5/1996 |
| JP | 09-183601 A | 7/1997 |
| JP | 2857045 B2 | 11/1998 |
| JP | 11-303792 A | 11/1999 |
| JP | 11-309328 A | 11/1999 |
| JP | 2000-516854 A | 12/2000 |
| JP | 2003-180836 A | 7/2003 |
| JP | 2004-085048 A | 3/2004 |
| JP | 2004-129761 A | 4/2004 |
| JP | 2005-087937 A | 4/2005 |
| JP | 2005 211392 A | 8/2005 |
| JP | 2006-062932 A | 3/2006 |
| WO | WO-98/28061 A1 | 2/1998 |

OTHER PUBLICATIONS

European Search Report of European Patent Application No. 07828860.2 dated Mar. 2, 2010 (EPO).

Office Action of Japanese Patent Application No. 2008-535423 mailed on Aug. 2, 2011 (Japan).

\* cited by examiner

| Adsorption cylinder A | | Adsorption step | Desorption step | Adsorption step | |
|---|---|---|---|---|---|
| Adsorption cylinder B | | Desorption step | Adsorption step | Desorption step | |

<Conventional art>

<Invention of present application>

Figure 6

OXYGEN CONCENTRATOR

TECHNICAL FIELD

The present invention relates to an oxygen concentrator to separate oxygen-enriched air or oxygen-concentrated gas from air for use.

BACKGROUND ART

In recent years, the number of patients suffering from chronic respiratory diseases such as pulmonary emphysema, pulmonary tuberculosis sequelae, chronic bronchitis and the like has tended to increase because of progress in aging and deterioration in living conditions. Oxygen inhalation therapy to inhale highly concentrated oxygen has been used as an effective treatment method for such patients. Oxygen inhalation therapy is a treatment method for patients with diseases described above to inhale an oxygen gas or oxygen-concentrated gas. A supply source of oxygen gas or oxygen-concentrated gas used in treatment includes a high pressure oxygen cylinder, a liquefied oxygen cylinder, an oxygen concentrator and the like, but the case using the oxygen concentrator has been increased because of durability in continuous use for a long period of time, easiness in use and the like.

The oxygen concentrator is an apparatus capable of separating oxygen from air to concentrate. As such an apparatus to separate and concentrate oxygen, an adsorption-type oxygen concentrator, equipped with a single or plural adsorption beds filled with adsorbents capable of selectively adsorbing nitrogen in air is widely known and used in hospitals and at homes from a standpoint of generating highly concentrated oxygen of 90% or higher. Among them, a pressure swing adsorption-type oxygen concentrator using a compressor as a pressure swing apparatus is widely used. Such an apparatus is an apparatus to generate highly concentrated oxygen continuously by repeating, at a certain cycle, an adsorption step to obtain unadsorbed and concentrated oxygen by supplying compressed air from a compressor to single or plural adsorption beds filled with adsorbents capable of selectively adsorbing nitrogen and adsorbing nitrogen on the adsorbents under the conditions in which inside of the adsorption beds is pressurized, and a desorption step to desorb nitrogen from the adsorbents by reducing the inner pressure of the adsorption beds to an atmospheric pressure or to a vacuum level for regeneration.

Measures to fine-tune a setting range of a volume of air to be supplied from a compressor to the adsorption beds or correct an adsorption-desorption sequence to tolerate a change of surrounding conditions, particularly temperature dependency of the adsorbents to maintain the oxygen concentration are adopted to respond to a decrease of an oxygen concentration in an oxygen-concentrated gas generated, which is caused by a change of environmental conditions such as variation in used temperature or barometric pressure in the oxygen concentrator or a decrease of the oxygen concentration in an oxygen-concentrated gas generated, which is caused by deterioration of the equipment with time.

Such an apparatus to maintain a product oxygen concentration is known, wherein a change of the oxygen concentration with time is corrected or a decrease of the oxygen concentration caused by deterioration of the equipment with time is compensated and the oxygen concentration of an oxygen-concentrated gas is maintained at a constant value by detecting the oxygen concentration of the oxygen-concentrated gas by using an oxygen sensor and performing feedback controls on an airflow volume of a compressor, a cycle timing of adsorption-desorption and the like (Japan Patent Application Laid-Open No. 2000-516854 and Japanese Patent Laid-open publication No. Laid-Open H09-183601).

DISCLOSURE OF INVENTION

An amount of oxygen prescribed, which is a flow rate of oxygen to supply from an oxygen concentrator to a user is determined by severity of patients to use it. Accordingly, an optimum apparatus to patients is chosen and supplied for use from various equipments including a low flow rate-type apparatus with a maximum possible supply flow rate of 2 L/min, 3 L/min and the like and a high flow rate-type apparatus with a maximum possible supply flow rate of 5 L/min, 7 L/min and 10 L/min and the like.

While the maximum supply flow rate of the apparatus is the value described above, an actual supply flow rate of oxygen clinically used can be generally set at a low flow rate of 0.25 L/min, 0.5 L/min and the like. In this case, where oxygen is generated at the maximum predetermined flow rate even if a prescribed flow rate is low, oxygen is wastefully generated and consuming more electric power. This leads to an effort to reduce electric power consumption in many apparatuses by an inverter control of a driving motor for a compressor to reduce a volume of raw material air to be supplied from the compressor to an adsorption bed.

When an attempt is made to secure a volume of raw material air required to supply concentrated oxygen in a high flow rate setting zone in a high flow rate-type apparatus, a volume of raw material air becomes excessive in a low flow rate setting zone to result in excess supply of the raw material. This leads to adsorption of part of oxygen in raw material air on the adsorbents to concentrate unadsorbed argon in the gas generated, as a result, an oxygen concentration in the oxygen concentrated gas generated is reduced.

A method of reducing a volume of raw material air supplied by lowering the number of revolution of a compressor is applied, but there exist such problems that as a control range in the number of revolution of the compressor is limited, and that its operation becomes unstable when a range in the number of revolution used is too low.

An object of the present invention is to solve the problems described above and to provide an oxygen concentrator having both functions, of which electric power consumption of the apparatus is reduced and an oxygen concentration in a low flow rate setting zone of an oxygen flow rate supplied from the oxygen concentrator is kept constant.

That is, the present invention provides an oxygen concentrator that is a pressure swing adsorption-type oxygen concentrator equipped with at least one adsorption bed filled with an adsorbent capable of selectively adsorbing nitrogen relative to oxygen, an air supply device to supply compressed air to the adsorption bed, a flow channel switching device to repeat at a predetermined timing an adsorption step to supply air from the air supply device to the adsorption bed to isolate concentrated oxygen and a desorption step to depressurize the adsorption bed to regenerate the adsorbent therein, and a flow rate setting device to set a volume of concentrated oxygen supplied to a user, comprising an exhaust pipe channel equipped with a leak valve in a flow channel between the air supply device and the adsorption bed to release a part of compressed air that is to be supplied to the adsorption bed into atmosphere.

The present invention also provides the oxygen concentrator comprising a control device to control an air supply volume from the air supply device based on a predetermined flow rate in the flow rate setting device, the air supply volume from the air supply device at a certain value when the predetermined flow rate is equal to or below a given flow rate, and a release volume of compressed air through the leak valve as determined based on the predetermined flow rate.

The present invention also provides the oxygen concentrator, wherein the exhaust pipe channel is branched from a pipe channel connecting the air supply device and the channel switching device and equipped with a flow rate control valve as the leak valve, and wherein the air supply device is a compressor with an inverter and the control device is to control the number of revolution of a compressor based on a predetermined value in the flow rate setting device, the number of revolution of the compressor at a certain value when a predetermined flow rate is equal to or below a given flow rate, and an open/shut operation of the leak valve to release from the exhaust pipe channel a certain release volume determined based on a predetermined value in the flow rate setting device.

The present invention also provides an oxygen concentrator that is a pressure swing adsorption-type oxygen concentrator equipped with at least one adsorption bed filled with an adsorbent capable of selectively adsorbing nitrogen relative to oxygen, an air supply device to supply compressed air to the adsorption bed, a flow channel switching device to repeat at a predetermined timing an adsorption step to supply air from the air supply device to the adsorption bed to isolate concentrated oxygen and a desorption step to depressurize the adsorption bed to regenerate the adsorbent therein, and a flow rate setting device to set a volume of concentrated oxygen supplied to a user,
comprising an air release function to release a part of compressed air that is to be supplied to the adsorption bed immediately before the completion of the adsorption step.

The present invention also provides the oxygen concentrator, wherein the flow channel switching device is equipped with a two-way electromagnetic valve (a) installed on a compressed air supply pipe connecting the air supply device and the adsorption bed, a branch pipe channel in the adsorption bed and an exhaust side installed in a downstream side of the two-way electromagnetic valve (a) and a two-way electromagnetic valve (b) installed on the branch pipe channel in the release side.

The present invention also provides the oxygen concentrator, wherein the adsorption bed is composed of two adsorption beds and the flow channel switching device is equipped with a branch pipe channel connecting the air supply device and each adsorption bed to supply compressed air, two-way electromagnetic valves (a1 and a2) installed on each branch pipe channel, a branch pipe channel in the adsorption bed and an exhaust side installed in a downstream side of the two-way electromagnetic valves (a1 and a2), two-way electromagnetic valves (b1 and b2) installed on each branch pipe channel in the exhaust side and a branch pipe channel connecting an exhaust outlet and the two-way electromagnetic valves (b1 and b2);
comprising a control device to control a switching timing of the flow channel switching device that determines a release volume of compressed air immediately before completion of an adsorption step, based on a predetermined value in a flow rate setting device.

BEST MODE FOR CARRYING OUT THE PRESENT INVENTION

Figure 1:
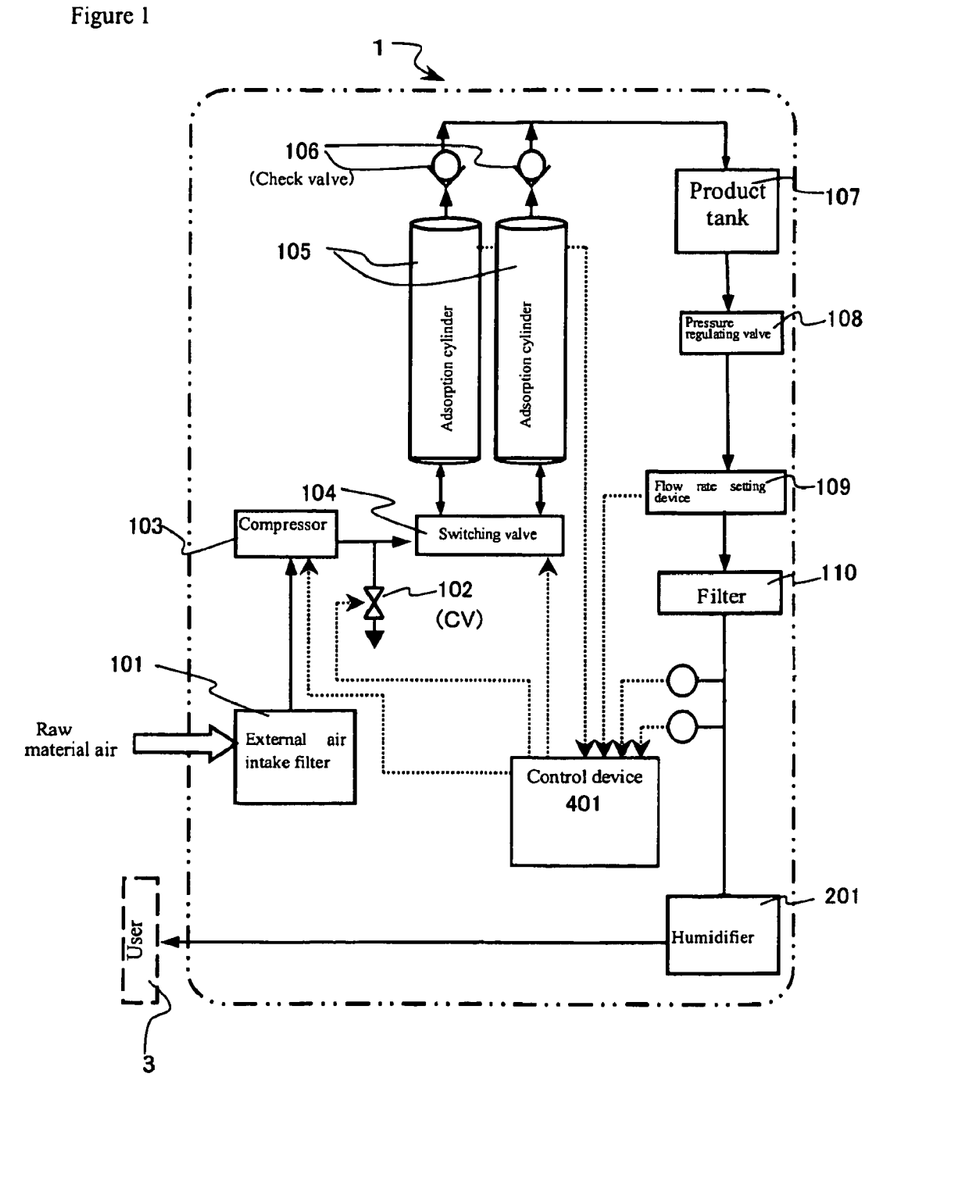
FIG. 1 is a schematic diagram of a pressure swing adsorption-type oxygen concentrator in an example of illustrative embodiment in the present invention.

An example of illustrative embodiment in an oxygen concentrator of the present invention is described using drawings below. FIG. 1 is a schematic constitutional diagram of an apparatus illustrating one embodiment of a pressure swing adsorption-type oxygen concentrator of the present invention. In FIG. 1, 1 and 3 represent an oxygen concentrator and a user (patient) inhaling humidified oxygen-enriched air, respectively. Pressure swing adsorption-type oxygen concentrator 1 is equipped with external air intake filter 101, compressor 103, switching valve 104, adsorption cylinder 105, check valve 106, product tank 107, pressure regulating valve 108, flow rate setting device 109 and filter 110. With this, oxygen-enriched air can be generated by concentrating an oxygen gas from raw material air brought in from outside.

Raw material air brought in an oxygen concentrator from atmosphere is first taken in from an air intake port equipped with external air intake filter 101 to eliminate foreign particles such as dust and the like into the apparatus as clean air not containing, from which coarse particulates, dusts and the like are eliminated. At this time, ordinary atmospheric air contains about 21% oxygen gas, about 77% nitrogen gas, 0.8% argon gas and 1.2% gases such as steam and the others. Such an oxygen concentrator selectively concentrates and isolates oxygen gas required for a breathing gas.

For isolating such oxygen gas, a pressure swing adsorption method is used, in which raw material air is pressurized by compressor 103 to supply the air to adsorption cylinder 105 filled with adsorbents containing zeolites and the like, which selectively adsorb nitrogen gas molecules relative to oxygen gas molecules by successively switching targeted adsorption cylinders 105 by switching valve 104, thereby about 77% nitrogen gas contained in raw material air inside adsorption cylinder 105 is selectively adsorbed and eliminated to take out unadsorbed oxygen gas from, one end of adsorption cylinder 105 into product tank 107.

Molecular sieve zeolites such as zeolite 5A, zeolite 13X, Li—X zeolite, MD-X zeolite and the like are used as an adsorbent selectively adsorbing nitrogen gas molecules relative to oxygen gas molecules.

Adsorption cylinder 105 described above is composed of a cylindrical vessel filled with the adsorbents described above and is generally available as a one cylinder-type apparatus, which uses one adsorption cylinder to a desorption step to intermittently generate oxygen by successively switching an adsorption step, a two cylinder-type apparatus using two adsorption cylinders, which uses two adsorption cylinders to continuously generate oxygen, by switching an adsorption step and a desorption step in such a way that, while the one adsorption cylinder is under an adsorption step, the other adsorption cylinder is under a desorption step, or further a multiple cylinder-type apparatus having three cylinders or more. Multiple cylinder-type with two cylinders or more of adsorption cylinders 105 is preferably used in order to continuously and effectively produce oxygen-enriched air from raw material air.

A rotating-type air compressor such as screw-type, rotary-type, scroll-type air compressors and the like may be used in some cases as compressor 103 described above in addition to a reciprocating-type air compressor. The power source of a motor to drive this compressor 103 may be alternate current or direct current.

An oxygen-concentrated gas containing an oxygen gas as a main component, which is not adsorbed in adsorption cylinder 105 described above, is flown into product tank 107 via check valve 106 that is installed to prevent the gas from flowing back into adsorption cylinder 105.

A nitrogen gas adsorbed on the adsorbents filled in adsorption cylinder 105 is now required to be desorbed from the adsorbents in order to reuse the adsorbents to adsorb the nitrogen gas again from freshly introduced raw material air. For this purpose, switching valve 104 is used to switch from a pressurized condition achieved by compressor 103 to a depressurized condition (for example, atmospheric pressure state or negative pressure state) to desorb the nitrogen gas adsorbed to regenerate the adsorbents. In this desorption step, an oxygen-concentrated gas may be flown back as a purge gas from the product outlet side of the adsorption cylinder during the adsorption step or from product tank 107 in order to increase a desorption efficiency.

An oxygen-concentrated gas is produced from raw material air and stored in product tank 107. The oxygen-concentrated gas stored in product tank 107 contains, for example, an oxygen gas highly concentrated to a level of 95%. Pressure regulating valve 108, flow rate setting device 109 and the like subsequently control the oxygen flow rate and pressure to supply to a user and feed to humidifier 201, from which a humidified oxygen-concentrated gas is supplied to patient 3.

Such a humidifier used may include a non-water supply humidifier without using water, in which an oxygen-concentrated gas in dry state is humidified by the moisture brought from external air using a moisture permeation membrane module having moisture permeation membranes; a bubbling-type humidifier using water for humidification; or a surface evaporation type humidifier.

A predetermined value on flow rate setting device 109 is detected to control the number of revolution in an electric motor for compressor 103 by control device 401 to control an airflow volume to be supplied to adsorption cylinder 105. For example, when a predetermined flow rate is set at a low flow rate, lowering the number of revolution in an electric motor for the compressor suppresses the volume of raw material air to be supplied and the amount of oxygen to be generated, leading to reduction of electric power consumption.

There exists a limit to control the number of revolution in a compressor so that lowering the number of revolution in the compressor more than necessary may result in unstable operation of the compressor, sometimes in its shutdown. Accordingly, control to reduce the number of revolution of compressor 103 has a limit no matter how a predetermined flow rate of oxygen in an oxygen concentrator is set at a low flow rate, resulting in operation at a constant speed of a lower operation limit in compressor 103 when the flow rate is equal to a given value or less.

Figure 2:
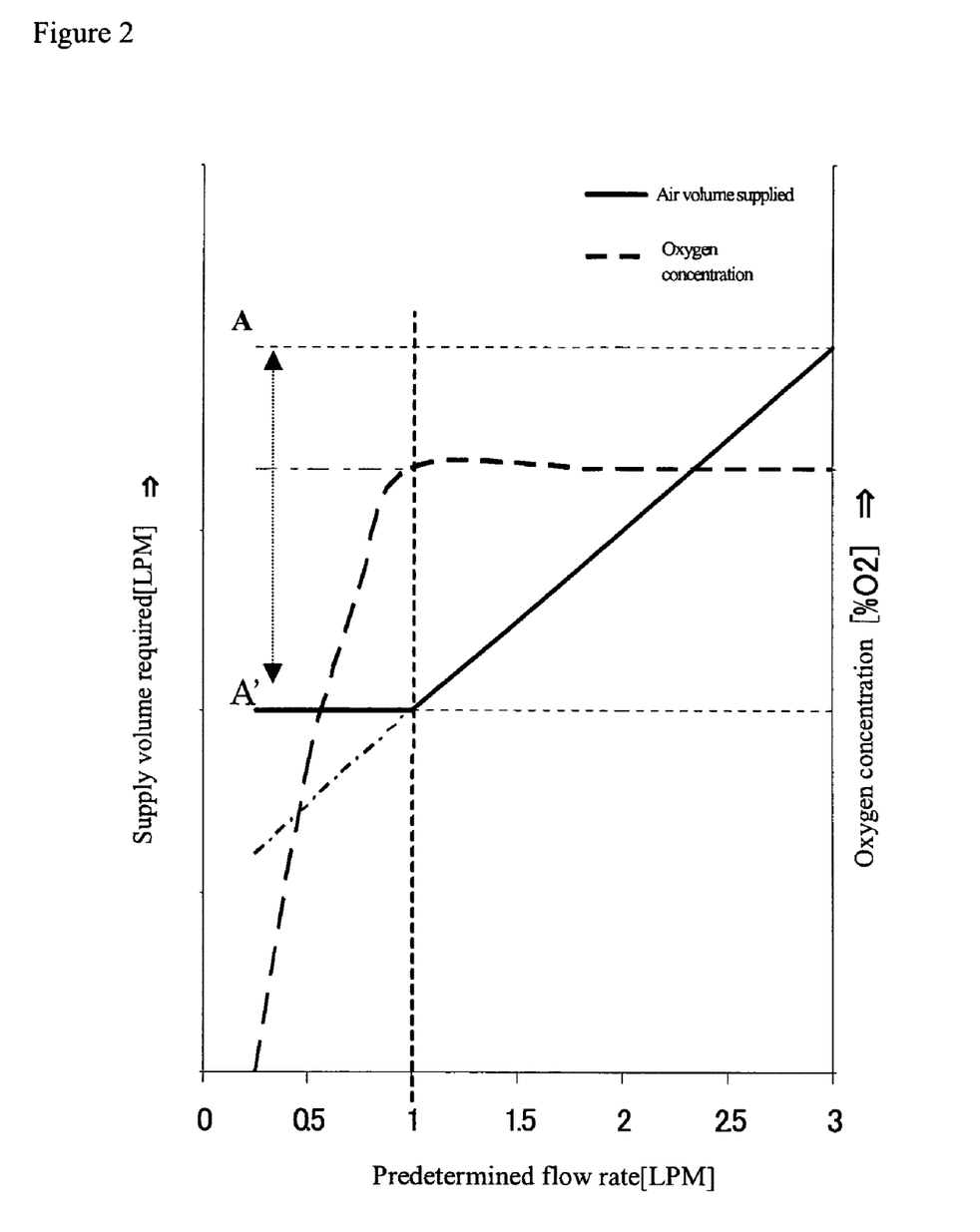
FIG. 2 is a diagram to demonstrate a relation of a concentration of oxygen generated with a supply volume of raw material air required for a predetermined flow rate in a conventional oxygen concentrator. A-A' represents a range of an airflow volume suppliable with a compressor and A' represents a lower limit of an airflow volume suppliable with a compressor.

As shown in FIG. 2, a range in which compressor 103 can stably supply compressed air is an A-A' range and the compressor is operated at a constant speed of lower limit A' when a range of a predetermined flow rate is equal to 1 L/min or less.

Adsorption cylinder 105 in an oxygen concentrator is designed to maintain an oxygen concentration at 90% or higher even at a maximum predetermined flow rate of the apparatus. Thus, when a volume of raw material air is excessively supplied to a certain level at a lower limit of compressor operation in a low flow rate zone of a predetermined oxygen flow rate even if a volume of oxygen isolated is low, not only nitrogen molecules but also oxygen molecules are adsorbed on adsorbents in adsorption cylinder 105, causing an excess adsorption phenomenon. As shown in a long dashed short dashed line of FIG. 2, the excess adsorption phenomenon can be prevented even at a predetermined flow rate of 1 L/min or less if a volume of airflow to be supplied by the compressor can be lowered, but the compressor cannot be stably driven at or below its rated conditions. As a result, the amount of oxygen generated in an oxygen-concentrated gas generated is reduced and the concentration of unadsorbed argon is increased, resulting in a phenomenon in which the oxygen concentration in the oxygen-concentrated gas is reduced in a low flow rate zone (at 1 L/min or less).

Figure 3:
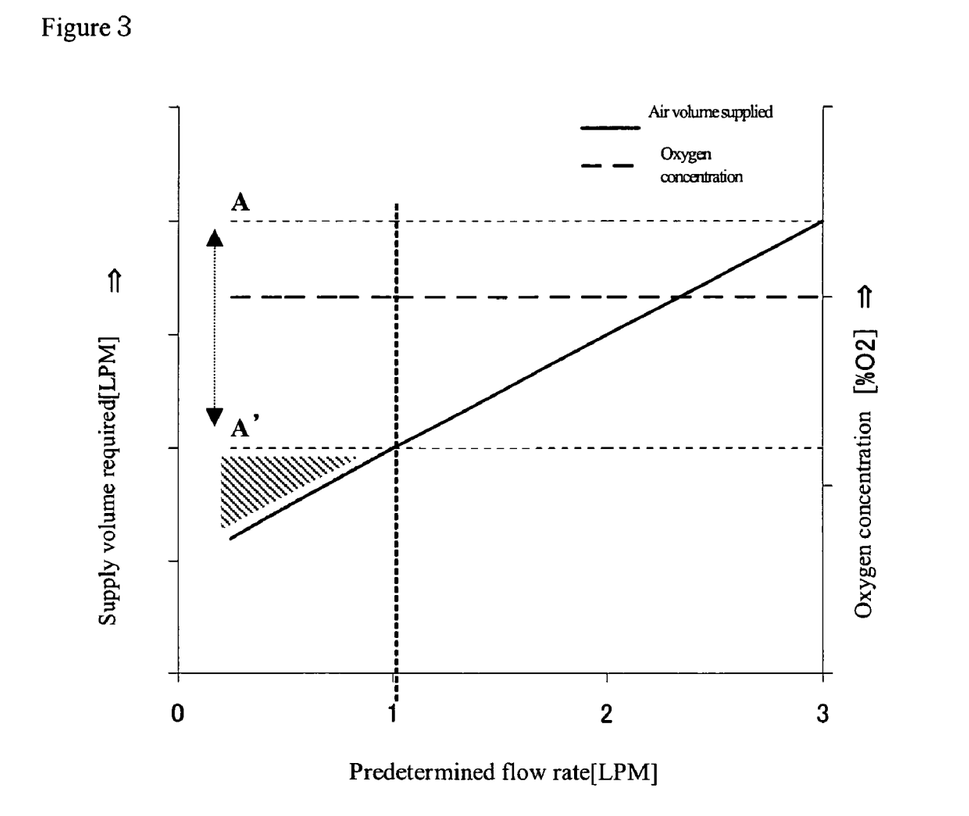
FIG. 3 is a diagram to demonstrate a relation of a concentration of oxygen generated with a supply volume of raw material air required for a predetermined flow rate in an oxygen concentrator in the present invention.

In order to prevent such excess adsorption phenomenon, an oxygen concentrator of the present invention is provided with a branch pipe equipped with leak valve 102 on a flow channel between compressor 103 and switching valve 104 to release excess raw material air. When a predetermined value of the flow rate setting device is equal to a certain value or less and the number of revolution in the compressor is controlled at a lower limit to enter into steady operation, leak valve 102 is opened to release excess raw material air relative to a supply volume required for raw material air. For using such leak valve 102, there may be used a method in which an excess amount of the raw material to be supplied is proportionally released by controlling a valve opening of a control valve against a predetermined flow rate, or a method in which an excess amount is released according to an opening time of an electromagnetic valve. By using such a control method, excess adsorption of oxygen can be prevented and raw material air excessively supplied can be released as shown in a shaded area of FIG. 3. As a result, the concentration of oxygen generated can be maintained at a constant rate irrespective of a predetermined flow rate.

Figure 4:
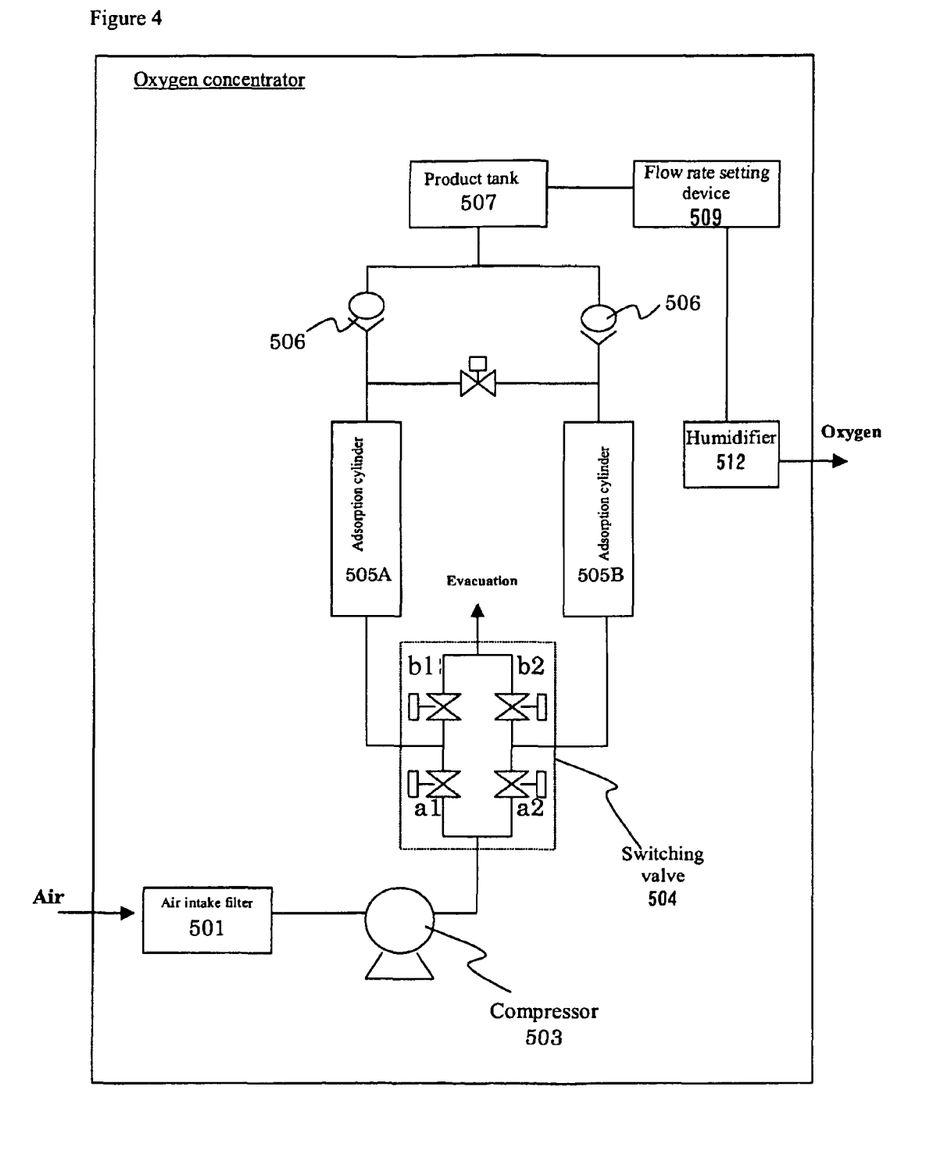
FIG. 4 is a schematic diagram of a pressure swing adsorption-type oxygen concentrator in another example of illustrative embodiment of the present invention.

FIG. 4 is a schematic constitutional diagram of an apparatus illustrating a pressure variable adsorption-type oxygen concentrator in another embodiment of the present invention.

As similar to the apparatus in FIG. 1, raw material air brought in from outside is entered in an air intake port equipped with external air intake filter 501 to eliminate foreign particles such as dust and the like. At this time, ordinary atmospheric air contains about 21% oxygen gas, about 77% nitrogen gas, 0.8% argon gas and 1.2% gases such as steam and the like. In such an apparatus only the oxygen gas required for a breathing gas is concentrated and isolated.

For isolating such an oxygen gas, raw material air is pressurized and supplied by compressor 503 into two adsorption cylinders 505A and 505B filled with adsorbents containing zeolites and the like, which selectively adsorb nitrogen gas molecules relative to oxygen gas molecules, by successively switching targeted adsorption cylinders by switching valve 504, and about 77% nitrogen gas contained in raw material air is selectively adsorbed and eliminated within the adsorption cylinders.

Oxygen-enriched air containing an oxygen gas as a main component, which is not adsorbed in the adsorption cylinders described above is flown into product tank 507 via check valve 506 installed to prevent the gas from flowing back into the adsorption cylinders.

A nitrogen gas adsorbed on the adsorbents filled in the adsorption cylinder is required to be desorbed from the adsorbents in order to reuse the adsorbents to adsorb a nitrogen gas again from freshly introduced raw material air. Thus, switching valve 504 switches from a pressurized condition achieved by compressor 503 to a depressurized condition (for example, atmospheric pressure state or negative pressure state) to desorb a nitrogen gas adsorbed to regenerate the adsorbents. In this desorption step, an oxygen-concentrated gas may be flown back as a purge gas from the product end side of the adsorption cylinder (or a product tank) in an adsorption step in order to increase a desorption efficiency.

An oxygen-concentrated gas is produced from raw material air to be stored in product tank 507. The oxygen-concentrated gas stored in product tank 507 contains, for example, an oxygen gas highly concentrated to a level of 95% and is supplied to humidifier 512 by controlling the flow rate and pressure with a pressure regulating valve, flow rate setting device 509 (CV: control valve) or the like to supply a humidified oxygen-concentrated gas to patients.

A predetermined value on flow rate setting device 509 is detected to control the number of revolution in an electric motor for compressor 503 by control device to control a volume of airflow to be supplied to adsorption cylinders. When a predetermined flow rate is set at a low flow rate, lowering the number of revolution suppresses the amount of oxygen generated, leading to reduction of electric power consumption. When a volume of raw material air is excessively supplied to a certain level at a lower limit of compressor operation, not only nitrogen molecules but also oxygen molecules are adsorbed on adsorbents in adsorption cylinders 505A and 505B to cause an excess adsorption phenomenon. In an oxygen concentrator of the present invention, in order to prevent such excess adsorption phenomenon, switching valve 504 is switched during the adsorption step to control a volume of raw material air to be supplied to the adsorption cylinders and excess raw material air is released.

In two cylinder-type oxygen concentrator, as for relevant switch valve 504 a structure in a combination of four two-way valves (two-way electromagnetic valves, a1, a2, b1 and b2) as shown in FIG. 4 is adopted. Each electromagnetic valve may be connected by tubing or branch tubing, or the four electromagnetic valves may be assembled into a manifold.

Figure 5:
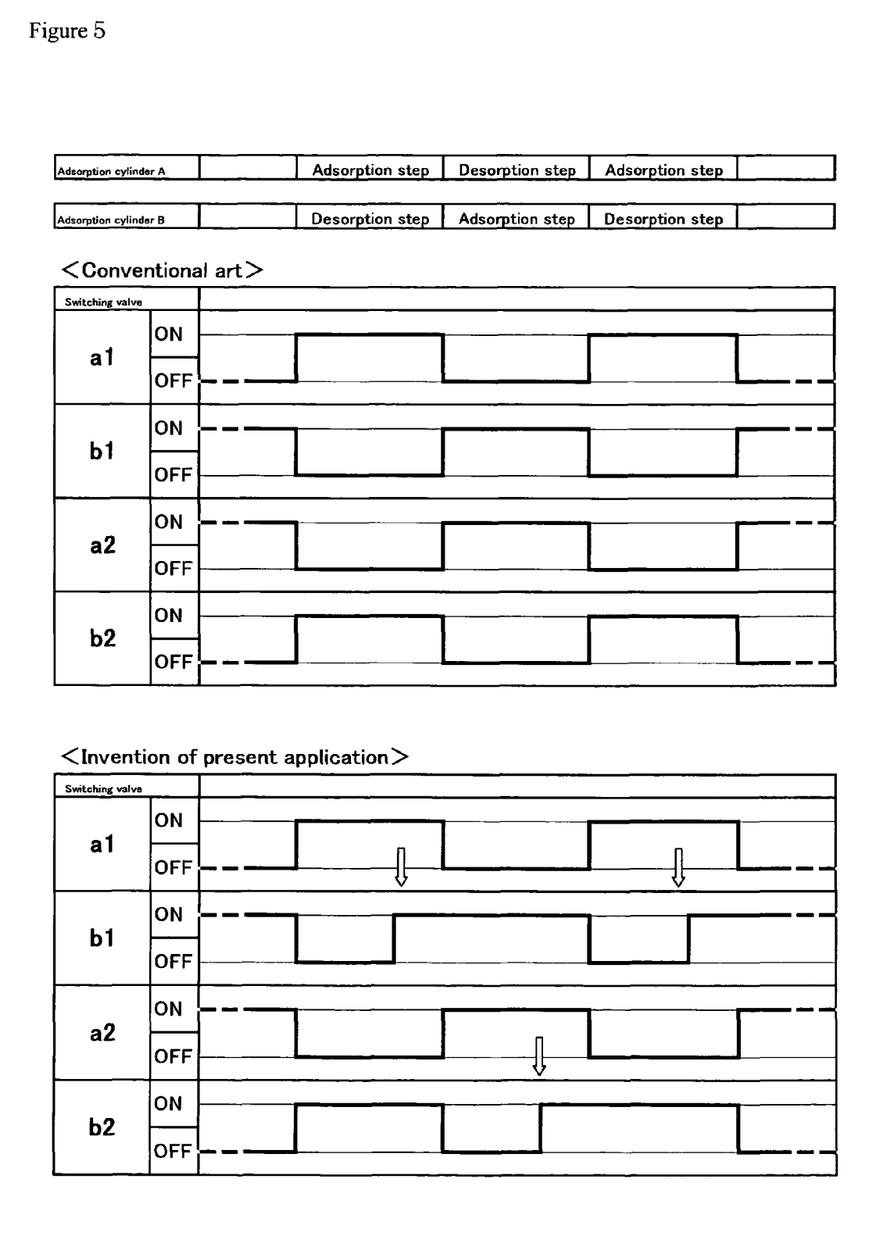
FIG. 5 is a schematic diagram to demonstrate the difference of a switching timing of a switch valve in the present invention with that in conventional art.

FIG. 5 demonstrates an open/shut timing of each two-way valve. When adsorption cylinder 505A is supplied with compressed air from a compressor in an adsorption step, generally the other adsorption cylinder 505B is in a desorption step and the adsorption cylinder under the pressurized condition is depressurized to release adsorbed nitrogen to atmosphere. At this time, two-way valve a1 is opened but two-way valves a2 and b1 are closed, thereby compressed air is supplied to adsorption cylinder 505A. At the same time, two-way valve b2 is opened to release a nitrogen-enriched gas in adsorption cylinder 505B. By switching this operation after a given time, the adsorption step and the desorption step are switched repeatedly between adsorption cylinders 505A and 505B.

On the contrary, an apparatus of the present invention opens two-way valve b1 at a late stage of the adsorption step in adsorption cylinder 505A to release part of compressed air supplied by compressor 503 from two-way valve b1 through an exhaust line. This can reduce the amount of raw material air supplied from two-way valve a1 to adsorption cylinder 505A, preventing a phenomenon of excess oxygen adsorption. Similarly, by opening two-way valve b2 at a late stage of the adsorption step in adsorption cylinder 505B, part of compressed air is released from two-way valve b2 through the exhaust line.

Control of switch valve 504 is determined according to a predetermined value of an oxygen supply flow rate and a switching timing is controlled according to a predetermined signal of flow rate setting device 509. For example, in an apparatus capable of supplying a flow rate of up to 3 L/min, when a predetermined value is equal to 1 L/min or more, the number of revolution of a motor for compressor 503 is controlled without changing the switching timing to control the supply volume of raw material air, whereas when a predetermined value is equal to 1 L/min or less, the timing to open two-way valves b1/b2 constituting switching valve 504 at a late stage of the adsorption step is controlled ahead of time, thus controlling the volume of raw material air to be supplied to each adsorption cylinder 505A and 505B.

When a two cylinder-type oxygen concentrator capable of supplying a supply flow rate described above up to 3 L/min in FIG. 4 is used under a repetitive sequence of an adsorption step and a desorption step every 15 seconds and at a predetermined oxygen flow rate of 3 L/min, an oxygen-concentrated gas containing 93% oxygen concentration is obtained, whereas when a predetermined oxygen flow rate used is 0.25 L/min, an oxygen concentration in the oxygen-concentrated gas generated is decreased from 93% to 88% because of excess adsorption of oxygen molecules on adsorbents and concentration of argon gas.

As shown in FIG. 5, in an apparatus of the present invention, when two-way valve b1 in switching valve 504 on the release side is opened five seconds earlier in the adsorption step of adsorption cylinder 505A and two-way valve b2 on the release side is opened five seconds earlier in the adsorption step of adsorption cylinder 505B, part of raw material air from compressor 503 to be supplied to the adsorption cylinder in the adsorption step is released. In this way, it is possible to maintain an oxygen concentration at 93% even when the apparatus is operated at a predetermined oxygen flow rate of 0.25 L/min.

A timing to open earlier may be controlled by proportionally adjusting a volume of raw material air to match a predetermined flow rate or controlled in a multistage way.

Figure 6:
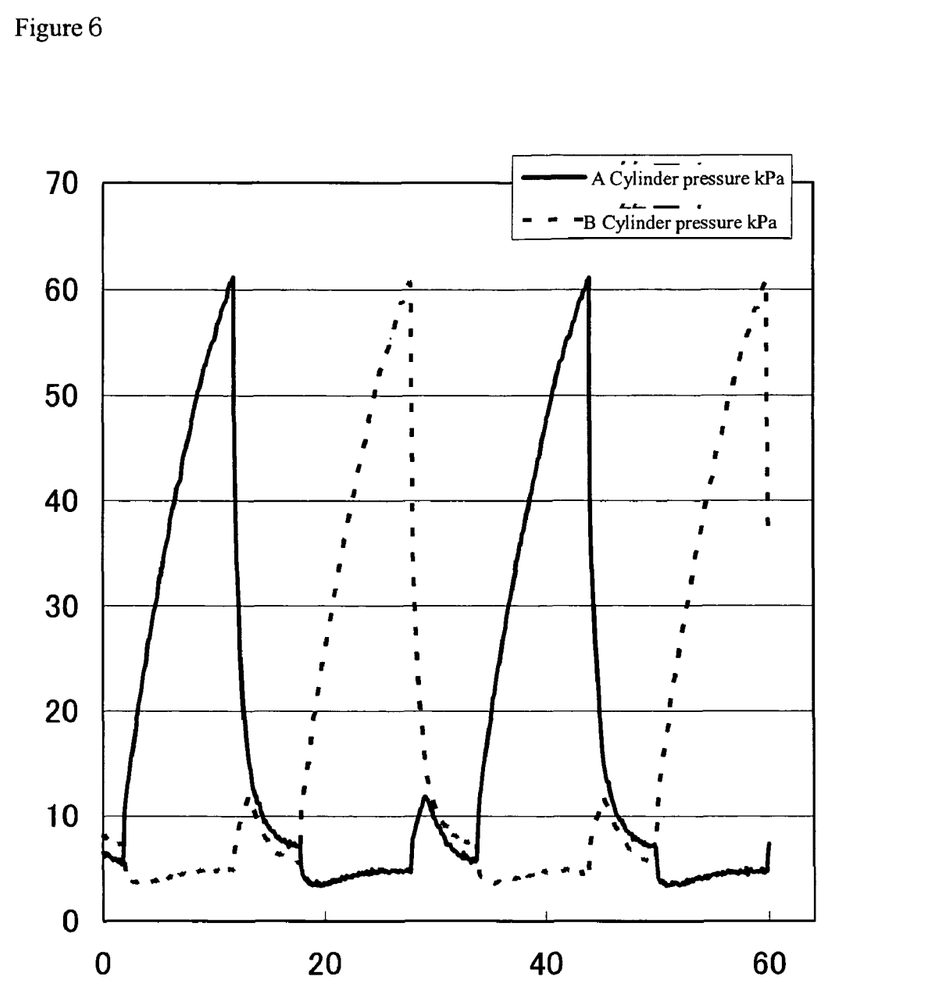
FIG. 6 is a diagram to demonstrate a pressure waveform in an adsorption cylinder in an oxygen concentrator of the present invention.

As shown in FIG. 6, a phenomenon is observed, in which part of a release gas is flown into an adsorption cylinder immediately before the completion of a desorption step, but has no effect on a concentration of oxygen generated and can conversely achieve reduction of electric power consumption because more than necessary increase of a pressure in the adsorption cylinder can be avoided.

EFFECT OF INVENTION

In an oxygen concentrator of the present invention, a leak valve (electromagnetic valve, control valve (CV) and the like)

is inserted between a compressor outlet and an inlet of an adsorption cylinder to release unnecessary raw material air, thus a concentration of oxygen generated is increased and a compressor can be stably driven without receiving any effects of surrounding conditions.

Further, when a predetermined value in a flow rate of oxygen supplied is in a low flow rate zone, by releasing unnecessary raw material air at a late stage of the adsorption step, it is possible to prevent excess adsorption of oxygen molecules caused by excess supply of raw material air and a decrease of oxygen concentration generated caused by concentration of argon. Further, even in a low flow rate zone, electric power consumption can be suppressed and operation of a compressor can be stabilized.

The invention claimed is:

1. A pressure swing adsorption-type oxygen concentrator including
    at least one adsorption bed filled with an adsorbent capable of selectively adsorbing nitrogen relative to oxygen,
    an air supply device to supply compressed air to the adsorption bed,
    a flow channel switching device to repeat at a predetermined timing an adsorption step to supply air from the air supply device to the adsorption bed to isolate concentrated oxygen and a desorption step to depressurize the adsorption bed to regenerate the adsorbent therein, and
    a flow rate setting device to set a volume of concentrated oxygen supplied to a user, comprising
    an exhaust pipe channel equipped with a leak valve in a flow channel between the air supply device and the adsorption bed to release a part of compressed air that is to be supplied to the adsorption bed into atmosphere, and
    a control device to control
    an air supply volume from the air supply device based on a predetermined flow rate in the flow rate setting device,
    the air supply volume from the air supply device at a certain value when the predetermined flow rate is equal to or below a given flow rate, and
    a release volume of compressed air through the leak valve as determined based on the predetermined flow rate.

2. The oxygen concentrator according to claim 1, wherein the exhaust pipe channel is branched from a pipe channel connecting the air supply device and the channel switching device and equipped with a flow rate control valve as the leak valve.

3. The oxygen concentrator according to claim 1, wherein the air supply device is a compressor with an inverter and the control device is to control
    the number of revolution of a compressor based on a predetermined value in the flow rate setting device,
    the number of revolution of the compressor at a certain value when a predetermined flow rate is equal to or below a given flow rate, and
    an open/shut operation of the leak valve to release from the exhaust pipe channel a certain release volume determined based on a predetermined value in the flow rate setting device.

4. A pressure swing adsorption-type oxygen concentrator including
    at least one adsorption bed filled with an adsorbent capable of selectively adsorbing nitrogen relative to oxygen,
    an air supply device to supply compressed air to the adsorption bed,
    a flow channel switching device to repeat at a predetermined timing an adsorption step to supply air from the air supply device to the adsorption bed to isolate concentrated oxygen and a desorption step to depressurize the adsorption bed to regenerate the adsorbent therein, and
    a flow rate setting device to set a volume of concentrated oxygen supplied to a user, comprising
    a control device comprising a control device to control a switching timing of the flow channel switching device that determines a release volume of compressed air immediately before completion of an adsorption step, based on a predetermined value in the flow rate setting device, and to release a part of compressed air that is to be supplied to the adsorption bed immediately before the completion of the adsorption step.

5. The oxygen concentrator according to claim 4, wherein the flow channel switching device comprises a two-way electromagnetic valve (a) installed on a compressed air supply pipe connecting the air supply device and the adsorption bed, a branch pipe channel between the adsorption bed and an exhaust side installed in a downstream side of the two-way electromagnetic valve (a) and a two-way electromagnetic valve (b) installed on the branch pipe channel in the release side.

6. The oxygen concentrator according to claim 4, wherein the adsorption bed is composed of two adsorption beds and the flow channel switching device comprises a branch pipe channel connecting the air supply device and each adsorption bed to supply compressed air, two-way electromagnetic valves (a1 and a2) installed on each branch pipe channel, a branch pipe channel in the adsorption bed and an exhaust side installed in a downstream side of the two-way electromagnetic valves (a1 and a2), two-way electromagnetic valves (b1 and b2) installed on each branch pipe channel in the exhaust side and a branch pipe channel connecting an exhaust outlet and the two-way electromagnetic valves (b1 and b2).

7. The oxygen concentrator according to claim 6, wherein the flow channel switching device comprises each manifold of a branch pipe channel connecting the air supply device and each adsorption bed to supply compressed air, two-way electromagnetic valves (a1 and a2) installed on each branch pipe channel, a branch pipe channel in the adsorption bed and an exhaust side installed in a downstream side of the two-way electromagnetic valves (a1 and a2), two-way electromagnetic valves (b1 and b2) installed on each branch pipe channel in the exhaust side and a branch pipe channel connecting an exhaust outlet and the two-way electromagnetic valves (b1 and b2).

* * * * *